US011130902B2

(12) United States Patent
Parini et al.

(10) Patent No.: US 11,130,902 B2
(45) Date of Patent: Sep. 28, 2021

(54) GAS HYDRATE INHIBITORS

(71) Applicant: Lamberti SPA, Albizzate (IT)

(72) Inventors: Mauro Parini, Houston, TX (US);
Andrea Balestrini, Sugar Land, TX (US); Lorenzo Giardini, Casella (IT);
Giovanni Floridi, Novara (IT);
Giuseppe Li Bassi, Gavirate (IT)

(73) Assignee: Lamberti SPA, Albizzate (IT)

( * ) Notice: Subject to any disclaimer, the term of this patent is extended or adjusted under 35 U.S.C. 154(b) by 247 days.

(21) Appl. No.: 16/445,632

(22) PCT Filed: Dec. 20, 2017

(86) PCT No.: PCT/EP2017/083935
§ 371 (c)(1),
(2) Date: Jun. 19, 2019

(87) PCT Pub. No.: WO2018/115191
PCT Pub. Date: Jun. 28, 2018

(65) Prior Publication Data
US 2019/0390100 A1 Dec. 26, 2019

(30) Foreign Application Priority Data
Dec. 23, 2016 (IT) .................. 102016000130571

(51) Int. Cl.
*C09K 8/52* (2006.01)
*C07C 229/12* (2006.01)
*C10L 3/10* (2006.01)

(52) U.S. Cl.
CPC ............. *C09K 8/52* (2013.01); *C07C 229/12* (2013.01); *C10L 3/107* (2013.01); *C09K 2208/22* (2013.01)

(58) Field of Classification Search
None
See application file for complete search history.

(56) References Cited

U.S. PATENT DOCUMENTS

| | | | |
|---|---|---|---|
| 5,460,728 A | 10/1995 | Klomp et al. | |
| 5,648,575 A | 7/1997 | Klomp et al. | |
| 6,214,091 B1 | 4/2001 | Klomp | |
| 6,596,911 B2 | 7/2003 | Przybylinski et al. | |
| 7,381,689 B2 | 6/2008 | Panchalingam et al. | |
| 8,034,748 B2 * | 10/2011 | Dahlmann | C07C 219/06 507/90 |
| 8,618,025 B2 * | 12/2013 | Webber | C07C 229/16 507/240 |
| 10,808,163 B2 * | 10/2020 | Lan | C09K 8/52 |
| 2005/0081432 A1 * | 4/2005 | Panchalingam | C10L 3/003 44/419 |
| 2020/0216742 A1 * | 7/2020 | Mohammed | C09K 8/36 |

FOREIGN PATENT DOCUMENTS

| | | |
|---|---|---|
| EP | 1450003 A1 | 8/2004 |
| EP | 1452580 A1 | 9/2004 |
| EP | 1717288 A2 | 11/2006 |
| WO | WO 2005/042675 A1 | 5/2005 |
| WO | WO 2015/015211 A1 | 2/2015 |
| WO | WO 2015/171106 A1 | 11/2015 |

OTHER PUBLICATIONS

International Search Report for PCT/EP2017/083928 dated Jun. 28, 2018.
Written Opinion of the international Search Authority for PCT/EP2017/083928 dated Jun. 28, 2018.

* cited by examiner

*Primary Examiner* — John J Figueroa
(74) *Attorney, Agent, or Firm* — Vorys, Sater, Seymour and Pease LLP; Iona Niven Kaiser

(57) ABSTRACT

The present invention relates to a method to inhibit gas hydrate formation in the field of crude oil and natural gas extraction, transportation and processing.

9 Claims, No Drawings

GAS HYDRATE INHIBITORS

CROSS REFERENCE TO RELATED APPLICATIONS

This application is the U.S. national phase of PCT/EP2017/083935 filed on Dec. 20, 2017, which claims priority to Italian patent application no. 102016000130571 filed on Dec. 23, 2016, the contents of both applications are hereby expressly incorporated by reference in their entireties herein.

FIELD OF THE INVENTION

The present invention relates to a method to inhibit gas hydrate formation in the field of oil and natural gas extraction, transportation and processing.

STATE OF THE ART

Gas hydrates (or clathrate hydrates, gas clathrates, clathrates, etc.) are crystalline water-based solids physically resembling ice, in which small non-polar hydrocarbon molecules (typically gases) are trapped inside "cages" of hydrogen bonded water molecules. In other words, gas hydrates are clathrate compounds in which the host molecule is water and the guest molecule is typically a hydrocarbon gas.

Gas hydrates cause problems for the petroleum industry because they can form solid crystals inside oil/gas pipelines, transfer lines, valves and other equipment. Since they have also a strong tendency to agglomerate and to adhere to the pipeline walls, the formation of gas hydrates may even result in obstructions of the pipelines. Preventing gas hydrate formation is therefore desirable in the art of producing, transporting and processing crude oil and natural gas.

One method to control the growth of gas hydrates is by employing chemicals that can lower the hydrate formation temperature and/or delay their formation (gas hydrate inhibitors). Different kinds of gas hydrate inhibitors exist: thermodynamic inhibitors and kinetic inhibitors/anti-agglomerants.

The most common thermodynamic inhibitors are lower alkyl alcohols and glycols.

Kinetic inhibitors and anti-agglomerants are also known as Low-Dosage-Hydrate-Inhibitors (LDHI), because they require much smaller concentrations than the conventional thermodynamic inhibitors. While kinetic inhibitors act by slowing down the kinetics of the nucleation, anti-agglomerants prevent the agglomeration (self adhesion) of gas hydrate crystals. Kinetic inhibitors are usually synthetic polymers or copolymers, while anti-agglomerants are often quaternary ammonium compounds ($R_1R_2R_3R_4N^+A^-$ where all of $R_1$, $R_2$, $R_3$ and $R_4$ are organic groups and $A^-$ is an anion) having surface active properties. These quaternary ammonium compounds and trialkyl amine salts with various substituents are described in many patents, such as in U.S. Pat. Nos. 5,460,728 5,648,575, 6,214,091 (Shell Oil Company, US), U.S. Pat. No. 6,596,911 (Baker Hughes Inc., US), U.S. Pat. No. 7,381,689 (Champion Technologies, Inc.), U.S. Pat. No. 8,034,748 (Clariant Produkte, DE).

In particular, U.S. Pat. No. 7,381,689 describes a method of controlling gas hydrate blockage through the addition, among the others, of amino or quaternary ammonium ester salts of formula:

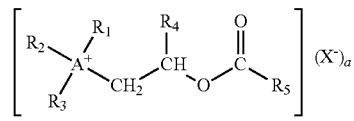

where: A is N; $R_1$ is a normal or branched alkyl group containing at least 4 carbon atoms; $R_2$ is hydrogen or an alkyl having from 1 to 4 carbon atoms; $R_4$ is selected from hydrogen, methyl and ethyl; $R_5$ is an organic moiety, such as an alkyl chain, containing from 4 to 20 carbon atoms; $(X^-)_a$ is an anion; and a is 0 or 1. When a is 1, then $R_3$ is selected from hydrogen, organic moieties having from 1 to 20 carbon atoms, and combinations thereof.

The $X^-$ anion can be selected from hydroxide, carboxylate, halide, such as chloride e bromide, sulfate, organic sulphonate, and combinations thereof. In the disclosure, many different quaternary ammonium bromide salts are exemplified, but, among them, there are no examples of quaternary ammonium ester salts.

Quaternary ammonium ester halides, have many advantages: they perform well at very low dosages, may be prepared from largely available, highly reactive, low cost, raw materials, such as alkyl and alkenyl bromide. Moreover they are ecologically friendly: in fact they are easily biodegraded in alkaline environments and exhibit low fish toxicity upon degradation. Unfortunately, quaternary ammonium halides have some drawbacks too.

First of all, quaternary ammonium halides undergo thermal decomposition. Two types of decomposition reactions usually take place simultaneously: the removal of one of the N-alk(en)yl groups as an alk(en)yl halide with formation of tertiary amines, and elimination of hydrogen halide through extraction of an hydrogen atom from one of the N-alk(en)yl groups with formation of mixture of tertiary amine halide salts and olefin. Although tertiary amine salts have been described as being effective as LDHI too, the unselective thermal decomposition often leads to low performing mixtures of compounds.

Moreover, halide ions in the presence of water are potentially damaging to metals because they may lead to the formation of hydro halogenic acid and to its accumulation. This can be an enormous problem in a field in which metal equipments constantly come into contact with water or with oil/water (possibly acidic) two-phase systems. This is particularly true for equipments which were not built in stainless steel or an high alloy steel or which were not treated for resisting to corrosive fluids, such as brines or seawater. Drums, transfer-lines, valves, tanks and injection systems, which are used for the storage, the preparation and the addition of the additives, are examples of these equipments.

The absence or the almost complete reduction of halide ions and organic halides in additives that are used at producing sites is therefore highly desirable in order to mitigate corrosion problems.

Finally, quaternary ammonium esters, also known as esterquats, are notorious surfactants and they are used in many field as foaming and emulsifying agents.

In the field of producing, transporting and processing crude oil, not only foaming is a problem which can slow down and reduce the efficiency of the processes, but also it can reduce the drainage, i.e. separation of water from the oil phase.

In addition, in the presence of a surfactant, oil and aqueous fluids may form emulsions that undesirably increase the viscosity of the mixture and thereby increase the power required to transport the oil. Finally, the produced hydrocarbons and the aqueous fluids must generally be separated, and where an emulsion has formed such separation may be very difficult.

It is an object of the present invention to provide a gas hydrate inhibitor based on a quaternary ammonium ester salt which do not contain halides and have very little tendency to metal corrosion and to stable foam/emulsion formation in comparison with the gas hydrate inhibitors of the prior art.

Now, it has been surprisingly found that using an alkyl sulfate or alkyl carbonate or carbonate salt of a quaternary ammonium ester with a relatively short fatty chain, it is possible to obtain an effective gas hydrate inhibition without the above mentioned problems.

As far as the Applicant knows, the use of these salts as gas hydrate inhibitors have never been described before.

DESCRIPTION OF THE INVENTION

It is, therefore, an object of the present invention, a method for inhibiting formation of gas hydrates in systems comprising mixture of hydrocarbons and water, said method comprising the addition to the mixture a quaternary ammonium ester salt of formula I:

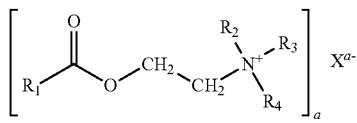

I wherein $R_1(CO)$— is the residue of a saturated or unsaturated, linear or branched fatty acid containing from 6 to 24, preferably from 6 to 20, more preferably from 8 to 18, carbon atoms;

$R_2$ and $R_3$ are, independently of each other, a butyl or a pentyl group;

$R_4$ is linear or branched alkyl group having from 1 to 5, preferably from 2 to 4, more preferably 2 or 3, carbon atoms;

X can be $R_4SO_4^-$, $R_4O(CO)O^-$, bicarbonate and carbonate;

a can be 1 or 2;

with the proviso that at least 50% by weight of the aliphatic carboxylic acid contains less than 16 carbon atoms.

DETAILED DESCRIPTION OF THE INVENTION

Preferably, $R_1(CO)$— is the residue of a saturated or unsaturated, linear or branched aliphatic carboxylic acid wherein at least 60% by weight of said acid contains less than 16 carbon atoms.

In a preferred embodiment of the method of the invention, $R_2$ and $R_3$ are the same and are a butyl group.

The quaternary ammonium ester salt of formula I of this invention can be prepared by quaternization of a tertiary amino ester of formula II:

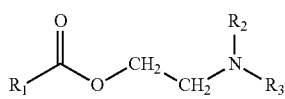

II wherein $R_1$, $R_2$ and $R_3$ have the same meaning as reported above.

The tertiary amino ester of formula II can be obtained by condensation of a saturated or unsaturated, linear or branched aliphatic carboxylic acid having formula $R_1COOH$, and a N,N-substituted ethanol amine is of formula $R_2R_3N$—$CH_2CH_2$—OH, wherein $R_2$ and $R_3$ are, independently of each other, a butyl or pentyl group.

Specific examples of saturated or unsaturated, linear or branched aliphatic carboxylic acids, suitable for the realization of the present invention, are 2-hexanoic acid, ethylhexanoic acid, n-octanoic acid, n-nonanoic acid, n-decanoic acid, n-undecanoic acid, n-dodecanoic acid, myristic acid, palmitic acid, palmitoleic acid, stearic acid, oleic acid, linoleic acid, linolenic acid and the like.

Also mixtures of these saturated or unsaturated, linear or branched aliphatic carboxylic acids can be used for the realization of the present invention. Suitable examples are the mixtures of carboxylic acids derived from natural oils, such as coco fatty acids, palm kernel fatty acids and palm fatty acids.

Preferred fatty acid are mixtures of fatty acids from natural oil and particularly preferred are palm kernel fatty acids and coco fatty acids, the latter being the most preferred.

The preferred N,N-substituted ethanol amine is N,N-dibutyl ethanol amine.

The preparation of carboxylic acid esters of alkanol amines is well known in the art. In an exemplary preparation process, the N,N-substituted ethanol amine is reacted with about 0.95 to about 1.1 molar equivalents of the carboxylic acid, ester or acid chloride, at a temperature ranging from about 90 to about 180° C. for about 1 to about 30 hours.

The process of preparation of the quaternary ammonium ester salt of formula I requires a further reaction step wherein the amino groups present in the molecule are substantially all quaternized. Quaternization is a reaction type that is well known in the art: typically it contemplates the reaction of the substrate with an alkylating agent.

For the quaternization step of the present invention, the alkylating agent can be selected from the group consisting of dialkyl sulfate and dialkyl carbonate, wherein the alkyl group has from 1 to 5 carbon atoms. Specific example of these alkylating agent are dimethyl sulfate, diethyl sulfate, dimethyl carbonate and diethyl carbonate, dipropyl sulfate, etc. The most preferred alkylating agents being diethyl sulfate and diethyl carbonate.

In one embodiment of the present invention, the tertiary amino ester of formula II is melt or dissolved in a suitable solvent, such as a $C_1$-$C_4$ alcohol or diol, and quaternized with about 0.95 to about 1.5 molar equivalents of a dialkyl sulfate to form the quaternized ammonium ester salt. The temperature is normally comprised between 70 and 140° C. Isopropanol, propylene glycol are the preferred solvents for the quaternization as they exhibit the best ability at reducing the viscosity of the quaternary salt solution.

The aforementioned quaternary ammonium ester salts of alkyl carbonates, carbonates and bicarbonates can be prepared by methods known in the art, such as those described in U.S. Pat. No. 5,438,034 and WO 03/006419.

It must be pointed out that the quaternary ammonium ester carbonates and bicarbonates of the invention are in equilibrium. The ratio bicarbonates/carbonates varies depending on the pH of the solution in which they are contained.

In one embodiment, the method of the present invention comprises the addition to the mixture of hydrocarbons and water of the quaternary ammonium ester salt as such, without any diluents or additives.

A another embodiment, the method of the present invention comprises the addition of a gas hydrate inhibitor composition, comprising the quaternary ammonium ester salt as herein described, a solvent (e.g. a liquid solvent) and other optional additives.

The gas hydrate inhibitor composition of the invention can comprise between 20 and 95% by weight, preferably between 45 an 90% by weight, more preferably 55 an 85% by weight of the quaternary ammonium ester salt.

Representative solvents suitable for formulation with gas hydrate inhibitor include polar solvents such as water, alcohols (including straight chain or branched aliphatic alcohols such as methanol, ethanol, 2-ethoxyethanol, propanol, isopropanol, butanol, isobutanol, hexanol), glycols and glycol ether derivatives (including ethylene glycol, propylene glycol, hexylene glycol, ethylene glycol monobutyl ether, ethylene glycol dibutyl ether, or diethylene glycol monomethyl ether), ethers (e.g., tetrahydrofuran), amides (e.g., N-methyl-2-pyrrolidinone or N,N-dimethylformamide), ketones (e.g. methyl ethyl ketone, cyclohexanone, or diisobutyl ketone); apolar solvents, such as aromatic hydrocarbon solvents (e.g. toluene and xylene) and mixtures thereof.

Preferred solvents are propylene glycol and isopropanol.

Suitable optional additives are paraffin inhibitors, asphaltene inhibitors, scale inhibitors, corrosion inhibitors, oxygen scavengers, hydrogen sulfide scavengers, non emulsifiers and emulsion breakers.

The quaternary ammonium ester salts, according to the present invention, are particularly suitable as gas-hydrate inhibitors when added to hydrocarbon fluids containing water.

They may be used by simple addition to the hydrocarbon fluids to be treated.

In the preferred procedure of this invention, the quaternary ammonium ester salt is added to a flowing hydrocarbon fluid which may contain both oil and water, at any point in a flow line upstream of the point or line that is intended to be protected. The dosage of gas hydrate inhibitor of the invention needed to obtain a sufficient protection varies with the application, but it is advantageously added in such an amount that the concentration is between 0.1 and 8.0% by weight, preferably between 0.5 and 5.0% by weight and more preferably between 1.0 and 3.5% by weight.

EXAMPLES

Gas Hydrate Inhibition Test

The performances of the gas hydrate inhibitors of the invention were evaluated with a Rocking Cell RC5 by PSL Systemtechnik.

Test Fluids

Hydrocarbon: Diesel

Aq. Phase: 4% wt seasalt water or deionized water

Gas: Mix of methane, ethane, propane and butane (various isomers)

Test Procedure

The sapphire test cells, containing a stainless steel ball, were filled with the fluids (see Table 1) and 2% by weight of inhibitor and pressurized with the gas mixture.

TABLE 1

|  | Inhibitor | Fluid (v/v) |
| --- | --- | --- |
| Test 1 | 2% | 50/50 4% wt seasalt water/diesel |
| Test 2 | 2% | 20/80 deionized water/diesel |

Each cell was the subjected to a cycle of cooling and rocking consisting of three steps: 1) flowing condition, 2) shut-in and 3) re-start flowing condition.

1) The pressurized cells were cooled down to 4° C. over a period of 5 hours while rocking. After reaching 4° C., the cells were rocked for 12 hours.
2) The rocking was stopped and the test cells were kept in horizontal position (shut-in) for 16 hours.
3) At the end of the shut-in period, rocking was re-started for 4 hours. Finally the cells were heated back up to 20° C.

At the beginning of the third step, the content of the cells was visually evaluated.

Each cycle was replicated three times and the results registered.

Results

The results of the gas hydrate inhibition tests (Table 2) are reported according to the following scale:

FAIL: The ball is stuck and/or large agglomerations or solid crystals and/or visible deposits on the cell walls.

PASS: The ball is free; solid crystals might be present, but agglomerates (large or small) break up with agitation.

TABLE 2

|  | Test 1 | Test 2 |
| --- | --- | --- |
| benzylcocodimethyl ammonium chloride* | FAIL | FAIL |
| N,N-dibutyl-N-Etyl-cocooxyethyl ammonium ethyl sulfate | PASS | PASS |

*Comparative

Foaming Power Tests

The foam volume (FV) and the foam stability (FS) were determined by stirring for 30 seconds at high speed (8000 rpm) with a Waring Blender 100 mL of a 1% by weight solution of the inhibitors in deionized water (Test 3) or in a 4% sea salt water solution (Test 4). The foamed composition is then transferred into a graded cylinder for the evaluation of the foam volume and the stability of the foam.

FV represent the volume in mL of foam at the end of the stirring. FS is the time in seconds required to the foamed solution to regenerate 50 mL of liquid. The longer the time, the higher the stability of the foam.

Table 3 shows the results of the foaming power test.

TABLE 3

|  | Test 3 | | Test 4 | |
| --- | --- | --- | --- | --- |
|  | FV | FS | FV | FS |
| benzylcocodimethyl ammonium chloride* | 480 | 260 | 430 | 215 |
| N,N-dibutyl-N-ethyl-soyaoxyethyl ammonium ethyl sulfate* | 320 | 180 | 230 | 118 |
| N,N-dibutyl-N-ethyl-cocooxyethyl ammonium chloride* | 210 | 97 | 172 | 59 |
| N,N-dibutyl-N-ethyl-cocooxyethyl ammonium ethyl sulfate | 185 | 70 | 160 | 46 |

*Comparative

The results demonstrate that the quaternary ammonium ester salts of formula I of the invention produce less foam than a ammonium salt of the prior art.

Corrosion Tests

The Linear Polarization Resistance (LPR) measurements were made with a Gamry Electrochemical Instrument system.

The LPR corrosion tests were conducted in 1 L Pyrex jacketed cells. 900 mL of synthetic brine (50/50 v/v 4.0% Seasalt water/Fresh Water) were loaded in the cell placed on a magnetic stirrer, deaerated overnight with $CO_2$ and, finally, saturated with 200 ppm $H_2S$ gas just before testing. A clean C1018 Mild Steel rod was inserted in the corrosion cell assembly as sample probe. A graphite rod was used as the counter electrode. The temperature of the solution was brought to 80° C. for the duration of the tests and $CO_2$ was continuously purged at a constant flow rate. The (Test 4) inhibitors were added at 10 ppm by volume of test solution.

The results are reported in Table 4 as % of protection after a fixed period of time compared to the blank, the test solution without any inhibitor, which is considered 100% corrosion.

TABLE 4

| | % Protection | |
|---|---|---|
| | 1 hour | 16 hours |
| benzylcocodimethyl ammonium chloride* | 79.7 | 89.5 |
| N,N-dibutyl-N-ethyl-cocooxyethyl ammonium chloride* | 78.9 | 87.9 |
| N,N-dibutyl-N-ethyl-cocooxyethyl ammonium ethyl sulfate | 81.4 | 90.2 |

*Comparative

The results demonstrate that the quaternary ammonium ester salts of formula I of the invention produce less corrosion than a ammonium chloride salt of the prior art.

The invention claimed is:

1. A method for inhibiting the formation of gas hydrates in systems comprising mixtures of hydrocarbons and water, said method comprising adding to the mixture a quaternary ammonium ester salt of formula I:

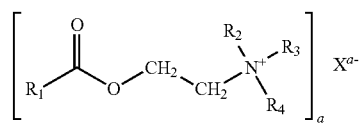

wherein
$R_1(CO)$— is the residue of a saturated or unsaturated, linear or branched fatty acid containing from 6 to 24 carbon atoms;
$R_2$ and $R_3$ are, independently of each other, a butyl or a pentyl group;
$R_4$ is linear or branched alkyl group having from 1 to 5 carbon atoms;
X can be $R_4SO_4^-$, $R_4O(CO)O^-$, bicarbonate and carbonate;
a can be 1 or 2;
with the proviso that at least 50% of the aliphatic carboxylic acid contains less than 16 carbon atoms.

2. The method of claim 1, wherein, in the quaternary ammonium ester salt of formula I, $R_1(CO)$— is the residue of a saturated or unsaturated, linear or branched aliphatic carboxylic acid wherein at least 60% by weight of said acid contains less than 16 carbon atoms.

3. The method of claim 1, wherein, in the quaternary ammonium ester salt of formula I, $R_2$ and $R_3$ are the same and are a butyl group.

4. The method of claim 1, wherein, in the quaternary ammonium ester salt of formula I, $R_4$ is linear or branched alkyl group having from 2 to 4 carbon atoms.

5. The method of claim 4, wherein $R_4$ is linear or branched alkyl group having 2 or 3 carbon atoms.

6. The method of claim 1, comprising adding to the mixture of hydrocarbons and water the quaternary ammonium ester salt of formula I as a composition comprising between 20 and 95% % by weight of said salt, a solvent and other optional additives.

7. The method of claim 6, wherein the composition comprises between 45 and 90% by weight of said quaternary ammonium ester salt.

8. The method of claim 1, comprising adding to the mixture of hydrocarbons and water between 0.1 and 8.0% by weight of quaternary ammonium ester salt of formula I.

9. The method of claim 8, comprising adding between 0.5 and 5.0% by weight of said quaternary ammonium ester salt.

* * * * *